(12) United States Patent
Tsuge et al.

(10) Patent No.: US 11,432,808 B2
(45) Date of Patent: Sep. 6, 2022

(54) GUIDE WIRE

(71) Applicant: ASAHI INTECC CO., LTD., Aichi (JP)

(72) Inventors: Kenta Tsuge, Seto (JP); Ayuko Miyata, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 0 days.

(21) Appl. No.: 16/846,445

(22) Filed: Apr. 13, 2020

(65) Prior Publication Data

US 2020/0237355 A1 Jul. 30, 2020

Related U.S. Application Data

(63) Continuation of application No. PCT/JP2017/037001, filed on Oct. 12, 2017.

(51) Int. Cl.
*A61B 17/00* (2006.01)
*A61B 17/12* (2006.01)

(52) U.S. Cl.
CPC .. *A61B 17/00234* (2013.01); *A61B 17/12022* (2013.01); *A61B 2017/00305* (2013.01);
(Continued)

(58) Field of Classification Search
CPC ........ A61B 17/00234; A61B 17/12022; A61B 2017/00305; A61B 2017/00331; A61B 2017/00336; A61B 2017/1205; A61M 2025/09083; A61M 2025/0915; A61M 2025/09175; A61M 25/09
See application file for complete search history.

(56) References Cited

U.S. PATENT DOCUMENTS

| 6,612,998 B2 | 9/2003 | Gosiengfiao et al. |
| 7,455,646 B2 | 11/2008 | Richardson et al. |

(Continued)

FOREIGN PATENT DOCUMENTS

| CN | 103830830 A | 6/2014 |
| EP | 2732846 A1 | 5/2014 |

(Continued)

OTHER PUBLICATIONS

U.S. Office Action dated Apr. 11, 2022, in related U.S. Appl. No. 16/846,446.

(Continued)

*Primary Examiner* — Mohamed G Gabr
(74) *Attorney, Agent, or Firm* — Xsensus LLP

(57) ABSTRACT

A guide wire of the present disclosure includes a core shaft having a distal end portion reducing in diameter, a coil body wound to cover the distal end portion, and a distal end fixing portion fixing the core shaft and the coil body to each other. The distal end portion includes a small diameter portion, a large diameter portion, and a tapered portion between the small diameter portion and the large diameter portion. The core shaft and the coil body are fixed at a portion excluding the tapered portion. A first bending rigidity FR1 of the large diameter portion, a second bending rigidity FR2 of the small diameter portion, and a length L of the tapered portion satisfy the following expressions (1) and (2). In the following expressions (1) and (2), the unit of L is mm (millimeter).

$$FR1/FR2 \geq 10 \quad (1)$$

$$1 \leq L \leq 3 \quad (2)$$

8 Claims, 6 Drawing Sheets

(52) U.S. Cl.
CPC ............... *A61B 2017/00331* (2013.01); *A61B 2017/00336* (2013.01); *A61B 2017/1205* (2013.01)

(56) References Cited

U.S. PATENT DOCUMENTS

| | | |
|---|---|---|
| 2003/0100848 A1 | 5/2003 | Gosiengfiao et al. |
| 2004/0106878 A1 | 6/2004 | Skujins et al. |
| 2007/0112282 A1 | 5/2007 | Skujins et al. |
| 2008/0262474 A1 | 10/2008 | Northrop |
| 2009/0227900 A1 | 9/2009 | Kim et al. |
| 2014/0142557 A1* | 5/2014 | Kosugi ............... A61B 17/3415 606/1 |
| 2014/0350519 A1 | 11/2014 | Urie |
| 2015/0148706 A1 | 5/2015 | Abner |
| 2016/0074631 A1* | 3/2016 | Otani ..................... B21F 3/02 140/71 C |
| 2016/0346518 A1 | 12/2016 | Terashi et al. |
| 2020/0237355 A1 | 7/2020 | Tsuge et al. |

FOREIGN PATENT DOCUMENTS

| | | |
|---|---|---|
| JP | 6-54912 A | 3/1994 |
| JP | 7-80076 A | 3/1995 |
| JP | 2010-524588 A | 7/2010 |
| JP | 2011-000469 A | 1/2011 |
| JP | 2016-221198 A | 12/2016 |
| JP | 2017-500925 A | 1/2017 |
| WO | 2010/108308 A1 | 9/2010 |
| WO | 2015/080948 A1 | 6/2015 |

OTHER PUBLICATIONS

International Search Report and Written Opinion dated Nov. 28, 2017 for PCT/JP2017/037001 filed on Oct. 12, 2017, 8 pages including English Translation of the International Search Report.

* cited by examiner

GUIDE WIRE

CROSS REFERENCE TO RELATED APPLICATION

This application is a continuation application of International Application No. PCT/JP2017/037001, filed Oct. 12, 2017. The contents of these applications are incorporated herein by reference in their entirety.

TECHNICAL FIELD

The present disclosure relates to a guide wire.

BACKGROUND

For example, when treating an occlusion site (for example, chronic total occlusion: CTO) in a blood vessel caused by the progress of calcification, a guide wire for guiding a treatment instrument such as a balloon catheter is inserted prior to the treatment instrument.

As such a guide wire to be inserted into a blood vessel or the like, there has been proposed a guide wire in which the distal end portion of a core shaft serving as an axis is stepwisely reduced in diameter so that the distal end can be flexibly bent in accordance with the shape of the inside of the blood vessel, according to WO 2015/080948.

In this technique, the distal end portion is stepwisely reduced in diameter, and thus has one or more inflection points. The distal side of the inflection point is bent, whereby the guide wire may advance along blood vessels having various shapes.

SUMMARY

However, when a guide wire is inserted into a blood vessel with a branch vessel or the like, the guide wire caught at the entrance of the branch vessel may come off the main vessel where the guide wire needs to advance, and enter deeply into the unintended branch vessel. Such aberrant insertion may cause unexpected complications, may take time to draw the aberrated guide wire back, causing delay in the procedure, or other problems.

The present disclosure has been made in view of the above circumstances, and an object of the present disclosure is to provide a guide wire capable of preventing breakage of the core shaft from the tapered portion as a starting point while suppressing aberrant insertion of the core shaft into a unintended branch vessel or other problems.

The present disclosure relates to a guide wire according to an embodiment of the present disclosure includes a core shaft that includes a distal end portion stepwisely decreasing in diameter toward a distal end direction, a coil body that is wound to cover at least a part of an outer periphery of the diameter-decreased distal end portion, and a distal end fixing portion that fixes the distal end of the core shaft and a distal end of the coil body to each other. The distal end portion of the core shaft includes a small diameter portion adjacent to the distal end fixing portion, a large diameter portion further in a proximal end direction than the small diameter portion and has a diameter larger than the small diameter portion, and a tapered portion between the small diameter portion and the large diameter portion. The tapered portion gradually increases in diameter from the small diameter portion toward the large diameter portion. The core shaft and the coil body are fixed at a portion of the core shaft excluding the tapered portion. A first bending rigidity FR1 of the large diameter portion, a second bending rigidity FR2 of the small diameter portion, and a length L of the tapered portion in an axial direction of the core shaft satisfy the following expressions (1) and (2), $$FR1/FR2 \geq 10 \quad (1)$$

$$1 \leq L \leq 3 \quad (2)$$

(in the above expressions (1) and (2), the unit of L is mm (millimeter).)

DETAILED DESCRIPTION

As used herein, an element or step recited in the singular and proceeded with the word "a" or "an" should be understood as not excluding plural elements, unless such exclusion is explicitly recited. Furthermore, references to "one embodiment" of the present invention are not intended to be interpreted as excluding the existence of additional embodiments that also incorporate the recited features.

Note that in the specification, "distal end direction" is a direction along the axial direction of the guide wire and indicates a direction of the side on which the distal end fixing portion is positioned relative to the large diameter portion of the core shaft. The "proximal end direction" is a direction along the axial direction of the guide wire and indicates the direction opposite to the distal end direction.

A guide wire of the present disclosure may include a core shaft that has a distal end portion stepwisely decreasing in diameter toward a distal end direction, a coil body wound to cover at least a part of an outer periphery of the diameter-decreased distal end portion, and a distal end fixing portion that fixes the distal end of the core shaft and a distal end of the coil body to each other. The distal end portion of the core shaft includes a small diameter portion adjacent to the distal end fixing portion, a large diameter portion further in a proximal end direction than the small diameter portion and has a diameter larger than that of the small diameter portion, and a tapered portion between the small diameter portion and the large diameter portion. The tapered portion gradually increases in diameter from the small diameter portion toward the large diameter portion. The core shaft and the coil body are fixed at a portion of the core shaft excluding the tapered portion. A first bending rigidity FR1 of the large diameter portion, a second bending rigidity FR2 of the small diameter portion, and a length L of the tapered portion in an axial direction of the core shaft satisfy the following expressions (1) and (2):

$$FR1/FR2 \geq 10 \quad (1)$$

$$1 \leq L \leq 3 \quad (2)$$

(in the above expressions (1) and (2), the unit of L is mm (millimeter).)

In this specification, a "main vessel" indicates a vessel extending in the same direction as the direction in which the distal end portion of the guide wire advances, and a "branch vessel" indicates a vessel having an opening facing the main vessel and extending diagonally relative to the direction in which the distal end of the guide wire advances.

Hereinafter, embodiments of the present disclosure will be described with reference to the enclosed drawings. However, the disclosure is not limited only to the embodiments illustrated in the drawings.

FIRST EMBODIMENT

Figure 1:
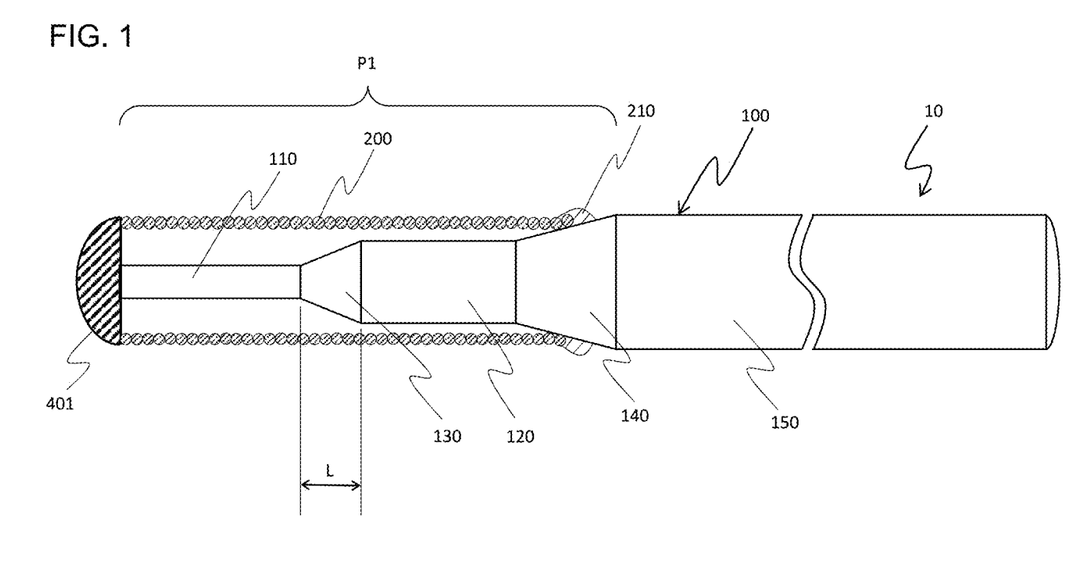
FIG. 1 is a schematic section view illustrating a guide wire, according to some embodiments of the present disclosure.

FIG. 1 is a schematic front view illustrating a guide wire, according to some embodiments of the present disclosure. A guide wire 10 roughly includes a core shaft 100, a coil body 200, and a distal end fixing part 401, as illustrated in FIG. 1.

The core shaft 100 has a distal end portion P1 stepwisely reducing or decreasing in diameter toward a distal end direction. The distal end portion P1 of the core shaft 100 includes a small diameter portion 110 adjacent to, e.g., continuous with, the distal end fixing portion 401 described later, a large diameter portion 120 that is positioned in a proximal end direction further than the small diameter portion 110 and has a larger outer diameter than an outer diameter of the small diameter portion 110, and a tapered portion 130 between, e.g., continuous with, the small diameter portion 110 and the large diameter portion 120 and gradually increases in diameter from the small diameter portion 110 toward the large diameter portion 120. In the embodiment, in a state where the core shaft 100 extends in a straight line, the section shape orthogonal to the axial direction of the core shaft 100 (cross-sectional shape) of each of the small diameter portion 110 and the large diameter portion 120 is circular with a certain diameter in the axial direction, and the section shape of the tapered portion 130 is a truncated conical shape. Further, the core shaft 100 includes a truncated conical connection portion 140 whose distal end is adjacent to, e.g., continuous with, the proximal end of the large diameter portion 120, and a core shaft main body 150 whose distal end is adjacent to, e.g., continuous with, the proximal end of the connection portion 140. In particular, the connection portion 140 may be tapered continuously with the large diameter portion 120 and the core shaft main body 150 and increases in diameter from the large diameter portion 120 toward the core shaft main body 150.

The total length of the core shaft 100 may be 1,800 to 3,000 mm, e.g., 1,900 to 2,500 mm. The axial length of the distal end portion P1 of the core shaft 100 may be 50 to 1,000 mm, e.g., 300 to 850 mm. The outer diameter of the core shaft main body 150 is normally 0.25 to 0.5 mm, and the outer diameter of the large diameter portion 120 is normally ⅕ to ⅔ of the core shaft main body 150. The outer diameter of the small diameter portion 110 is selected as described below.

Here, the outer diameters of the large diameter portion 120 and the small diameter portion 110 and a length L of the tapered portion 130 are selected so that the first bending rigidity FR1 of the large diameter portion 120, the second bending rigidity FR2 of the small diameter portion 110, and the length L of the tapered portion 130 in the axial direction of the core shaft satisfy the following expressions (1) and (2). In the following expressions (1) and (2), the unit of L is mm (millimeter).

$$FR1/FR2 \geq 10 \quad (1)$$

$$1 \leq L \leq 3 \quad (2)$$

Here, the ratio of the bending rigidity (FR1/FR2) between the large diameter portion 120 and the small diameter portion 110 in the above-described expression (1) is calculated as the ratio of the fourth power of the outer diameter using Hooke's law, for example, if the core shaft 100 is formed homogeneously.

In the embodiment, the entire length is 1,900 mm, the axial length of the distal end portion P1 is 100 mm (the axial length of the small diameter portion 110 is 10 mm, the axial length of the tapered portion 130 is 1 mm, the axial length of the large diameter portion 120 is 60 mm), the outer diameter of the core shaft main body 150 is 0.35 mm, the outer diameter of the large diameter portion 120 is 0.10 mm, and the outer diameter of the small diameter portion 110 is 0.04 mm, as an example.

The material forming the core shaft 100 is not particularly limited as long as the flexibility of the small diameter portion 110 is secured and the material has antithrombogenicity and biocompatibility. For example, the core shaft may include stainless steel such as SUS304, a superelastic alloy such as a Ni—Ti alloy, or the like.

The coil body 200 is wound so as to cover at least a part of the outer periphery of the distal end portion P1 that is reduced in diameter. For example, the coil body 200 is formed as a single spiral coil using one single wire spirally wound so that the adjacent wires are in contact with each other.

Further, the coil body 200 and the above-described core shaft 100 are not particularly limited as long as they are fixed at a portion of the core shaft 100 excluding the tapered portion 130. However, from the viewpoint of improving the bendability of the distal end portion P1, they may be fixed at a portion of the core shaft 100 excluding the small diameter portion 110 and the tapered portion 130, e.g., at a portion of the core shaft 100 excluding the small diameter portion 110, the large diameter portion 120, and the tapered portion 130. Specifically, as illustrated in FIG. 1, the coil body 200 and the core shaft 100 are brazed at two positions of between a distal end of the coil body 200 and a distal end of the core shaft 100 (see the distal end fixing portion 401), and between a proximal end of the coil body 200 and the connection portion 140 of the core shaft 100 (see the brazing portion 210), for example.

Examples of the brazing material used for brazing the coil body 200 include metals such as an Sn—Pb alloy, a Pb—Ag alloy, an Sn—Ag alloy, an Au—Sn alloy, or the like.

The diameter of the wire forming the coil body 200 may be 0.01 to 0.10 mm, e.g., 0.01 to 0.08 mm. The embodiment exemplifies the coil body 200 having a diameter of 0.06 mm.

The material of the wire forming the coil body 200 is not particularly limited as long as the flexibility of the small diameter portion 110 is secured and the material has anti-thrombogenicity and biocompatibility. For example, the wire may be stainless steel such as SUS316; a superelastic alloy such as a Ni—Ti alloy; a radiopaque metal such as platinum or tungsten, or the like.

The distal fixing portion 401 is a portion where the distal end of the core shaft 100 and the distal end of the coil body 200 are fixed to each other. Specifically, as described above, the distal end fixing portion 401 is a portion where the distal end of the core shaft 100 and the distal end of the coil body 200 are brazed, for example, and the distal end direction thereof is formed in a smoothly bent hemispherical shape by the above-described brazing material in order to prevent damages to the inner wall of a blood vessel when the guide wire 10 advances in the blood vessel.

Next, a use mode of the guide wire 10 will be described. First, the guide wire 10 is inserted into a blood vessel from the distal end portion P1 and is advanced along the blood vessel. Next, after the distal end of guide wire 10 is inserted into a branch portion of the blood vessel, it is pushed forward along the main vessel. Here, even if the distal end of the guide wire 10 is caught by the entrance of the branch vessel, the guide wire 10 does not enter deeply into the branch vessel and advances in the main vessel without breakage of the core shaft 100. Next, after the guide wire 10 reaches a treatment site, a treatment instrument, e.g., a balloon catheter, a stent, or the like, is conveyed along the guide wire 10, and various treatments are performed at the treatment site. After the treatments are completed, the guide wire 10 is withdrawn from the body by retrograding through the blood vessel, and a series of procedures is completed.

As described above, since the guide wire 10 has the above-described configuration, aberrant insertion of the core shaft 100 into the branch vessel may be prevented while also preventing breakage of the core shaft 100 from the tapered portion 130 as a starting point. As a result, procedures may be performed quickly and securely by smooth operation of the guide wire 10. Without be bound by theory, this is due to a combination of suppression of stress concentration on the tapered portion 130 during bending, that the core shaft 100 and the coil body 200 are not fixed at the tapered portion 130, and bending controllability of the distal end portion P1 by appropriate bending rigidity ratio of the small diameter portion 110 and the large diameter portion 120 (see expressions (1) and (2)).

In this manner, the guide wire 10 exerts the above-described effect, and thus may be used as a medical guide wire used for treatment in a blood vessel, for example.

Figure 2:
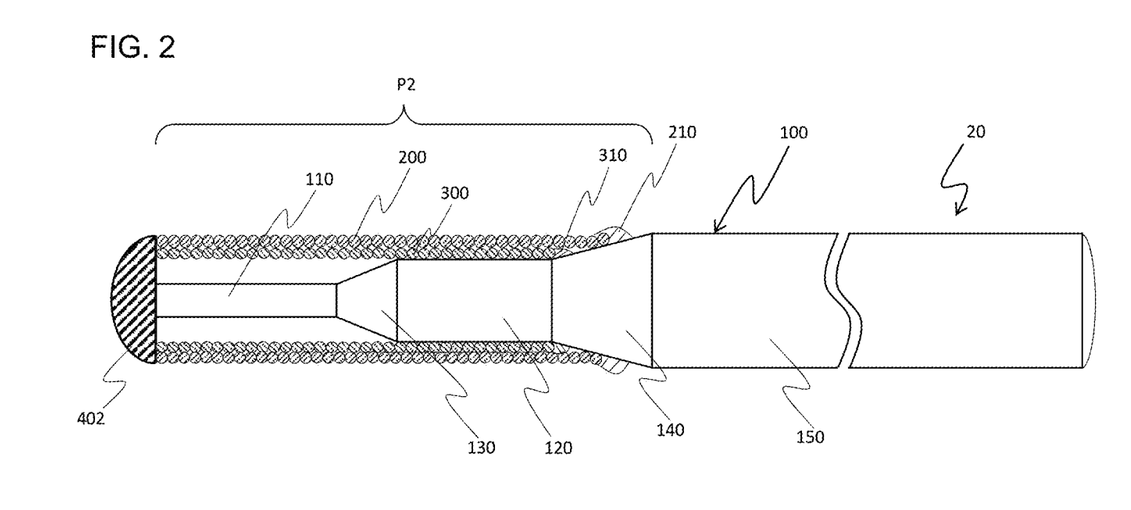
FIG. 2 is a schematic section view illustrating another guide wire, according to some embodiments of the present disclosure.

FIG. 2 is a schematic section view illustrating another embodiment of the present disclosure. As illustrated in FIG. 2, a guide wire 20 roughly includes the core shaft 100, the coil body 200, an inner coil body 300, and a distal end fixing portion 402. The guide wire 20 is different from the guide wire 10 in that the inner coil body 300 and the distal end fixing portion 402 are provided. Since the configurations of the core shaft 100, the coil body 200, and other components are the same as those in the description on the guide wire 10, the same parts are represented by the same reference numerals, and detailed description thereof will not be repeated.

The inner coil body 300 is a multiple spiral coil body inside the coil body 200 so as to cover the core shaft 100, and is formed as a multiple spiral using, for example, a hollow twisted wire (a bundle of wires in which a plurality of wires are previously twisted mutually) wound so that the adjacent wires are in contact with each other, and is arranged such that the inner periphery thereof is adjacent to, e.g., in contact with, the outer periphery of the large diameter portion 120.

In addition, the inner coil body 300 and the core shaft 100 are not particularly limited as long as they are fixed at a portion excluding the tapered portion 130, the portion being on the core shaft 100 in the proximal end direction than the tapered portion 130, and at the distal end fixing portion 402. For example, the inner coil body 300 may be fixed at a portion on the core shaft 100 in the proximal end direction further than the large diameter portion 120 and at the distal end fixing portion 402. As illustrated in FIG. 2, the inner coil body 300 and the core shaft 100 are brazed at two positions of between a distal end of the inner coil body 300 and the distal ends of the core shaft 100 and the coil body 200 (see the distal end fixing portion 402), and between a proximal end of the inner coil body 300 and the connection portion 140 of the core shaft 100 (see the brazing portion 310), for example.

Note that, the brazing material used for brazing the inner coil body 300 may include the same brazing material as the brazing material used for brazing the coil body 200 in the guide wire 10, for example.

The diameter of the wire forming the inner coil body 300 may be 0.01 to 0.05 mm, e.g., 0.01 to 0.04 mm. The embodiment exemplifies the inner coil body 300 having a diameter of 0.030 mm.

The material of the wire forming the inner coil body 300 may include the same material as the material of the wire of the coil body 200 described above in the description on the guide wire 10, for example.

The distal fixing portion 402 is a portion where the distal end of the core shaft 100, the distal end of the coil body 200, and the inner coil body 300 are fixed to one another. Specifically, as described above, the distal end fixing portion 402 is a portion where the distal end of the core shaft 100, the distal end of the coil body 200, and the distal end of the inner coil body 300 are brazed, and the distal end direction thereof is formed in a smoothly bent hemispherical shape by the brazing material, for example.

Since the use mode of the guide wire 20 is the same as that of the guide wire 10, the description of the guide wire 10 is not repeated.

In this manner, in the guide wire 20, the core shaft 100, and the inner coil body 300 are fixed at a portion excluding the tapered portion 130, the portion being on the core shaft 100 in the proximal end direction than the tapered portion 130, and at the distal end fixing portion 402. Therefore, even if the core shaft 100 is broken at the small diameter portion 110 or the tapered portion 130, the broken portion is connected to other portions of the guide wire 20 through the inner coil body 300, which prevents splitting or detachment of these portions, allowing the procedure to be performed more safely.

Note that the present disclosure is not limited to the configurations of the above-described embodiments, but is defined by the terms of the claims and is intended to include any modifications within the scope and meaning equivalent to the terms of the claims.

For example, the above embodiments have described the guide wires 10, 20 in which the rigidity of each of the coil body 200 and the inner coil body 300 is uniform. However, the bending rigidity of the coil body 200 and/or the inner coil body 300 may be higher in the proximal end direction than in the distal end direction of the tapered portion in the axial direction of the core shaft. Thus, the rigidity of the guide wire may largely be changed at the tapered portion. Thus, branch vessel aberrant insertion prevention may be enhanced. The coil body 200 and the inner coil body 300 as described above include those in which the wire diameters of the constituent wires are different before and after the tapered portion and in which the constituent wires in a portion in the proximal end direction than the tapered portion as a starting point are integrated by welding, soldering, or the like, for example.

Further, the above embodiment has described the guide wires 10, 20 in which the cross-sectional shape of the small diameter portion 110 is circular. However, for the purpose of improving the blood vessel selectivity, the cross-sectional shape of the distal end portion of the small diameter portion may be a substantially flat shape or a substantially flat plate shape, e.g., may be elliptical rather than circular.

Further, the above embodiments have described the guide wires 10, 20 in which the bending rigidity FR1 and FR2 are calculated using Hooke's law. However, the bending rigidity FR1 and FR2 may be values obtained by actual measurement or by a method other than the above-described methods.

The above embodiments have described the guide wires 10 in which the core shaft 100 and the coil body 200 are brazed, and the guide wire 20 in which the core shaft 100, the coil body 200, and the inner coil body 300 are brazed. However, the guide wire may be formed such that the above-described members are fixed by another known technique, e.g., arc welding, resistance welding, or the like.

Further, the above embodiments have described the guide wires 10 in which the core shaft 100 and the coil body 200 are fixed at the distal end fixing portion 401 and at the brazing portion 210, and the guide wire 20 in which the core shaft 100 and the inner coil body 300 are fixed at the distal end fixing portion 402 and at the brazing portion 310. However, the guide wire may be formed such that the above-described members are fixed at any one or two or more portions as long as such portions exclude the tapered portion.

Moreover, the above-described embodiments have described the guide wires 10, 20 in which the coil body 200 is formed as a single spiral coil and the inner coil body 300 is formed as a multiple spiral coil. However, the coil body 200 may be formed as a multiple spiral coil and the inner coil body 300 may be formed as a single spiral coil.

Further, the above-described embodiments have exemplified the guide wires 10, 20 including the connection portion 140 between the large diameter portion 120 and the core shaft main body 150 of the core shaft 100. However, the guide wire may be formed such that the large diameter portion is a part of the core shaft main body (the guide wire in which the large diameter portion and the core shaft main body have the same diameter and are continuous with each other).

EXAMPLES

Hereinafter, the disclosure will be concretely described based on examples, but the disclosure is not limited to these examples. These examples show the results regarding guide wires including the core shaft, the coil body, and the distal end fixing portion as described above in the description on the guide wire 10.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

<Guide Wire>

Regarding the specifications of each guide wire to be evaluated, Tables 1 and 2 show the outer diameter D1 of the small diameter portion, the outer diameter D2 of the large diameter portion, and the value of (FR1/FR2). Note that the above-described FR1 and FR2 have the same meaning as those in the above-described expression (1). Other specifications are as follows.

```
[Core shaft]
  - Material        : SUS304
  - Axial length
      Entire length               : 1,900 mm
      Distal end portion          : 100 mm
      Small diameter portion      : 10 mm
      Tapered portion             : Shown in Tables 1, 2
      Large diameter portion      : 60 mm
  - Diameter
      Core shaft main body: 0.35mm
      Small diameter portion      : Shown in Tables 1, 2
      Large diameter portion      : Shown in Tables 1, 2
[Coil body]
  - Material        : SUS304
  - Diameter        : 0.06 mm
```

<Evaluation>

Using each of the guide wires shown in Tables 1, 2, the branch vessel aberrant insertion property was evaluated by the following method. The results are shown in Tables 1, 2 and FIG. 4. In Tables 1, 2, the bending rigidity ratio (FR1/FR2) is calculated using bending rigidity obtained by Hooke's law.

[Branch Vessel Aberrant Insertion Prevention Property]

There were preliminarily prepared a guide wire bent in a U-shape at the middle of the small diameter portion as a starting point (a bent portion), and a hollow transparent acrylic plate that includes a straight main tube and a branch tube with an opening formed in the middle of the main tube to be diagonal with 75° relative to the main tube.

Figure 3A:
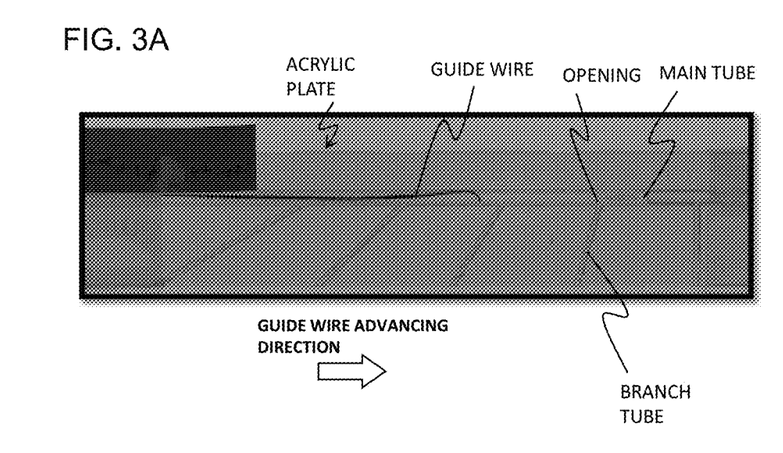
FIG. 3A is a schematic diagram illustrating a state of an advancing guide wire, and is the schematic diagram illustrating a state before a distal end of the guide wire reaches an opening of a branch vessel.

Next, using the guide wire and the acrylic plate, each guide wire is inserted into the main tube of the acrylic plate (see FIG. 3A, for example), and is further pushed forward after the distal end of the guide wire is hooked on the opening of the branch tube. Then, it was visually observed whether the guide wire would enter deeply into the branch tube from the opening.

Figure 3B:
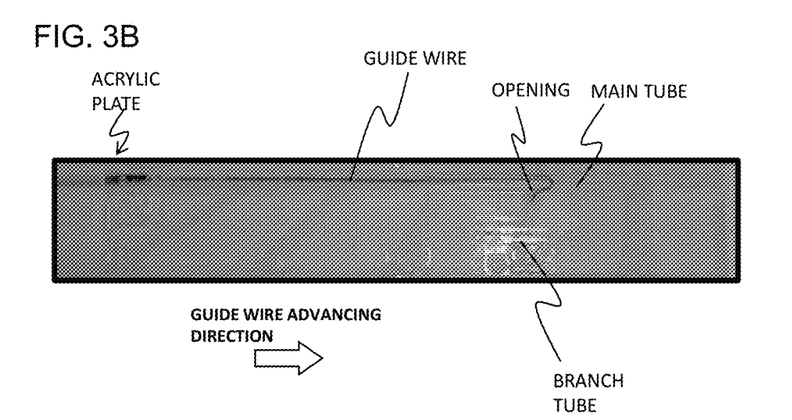
FIG. 3B is a schematic view illustrating a state of an advancing guide wire, and is the schematic view illustrating the guide wire having a preferable branch vessel aberrant insertion prevention property.
Figure 3C:
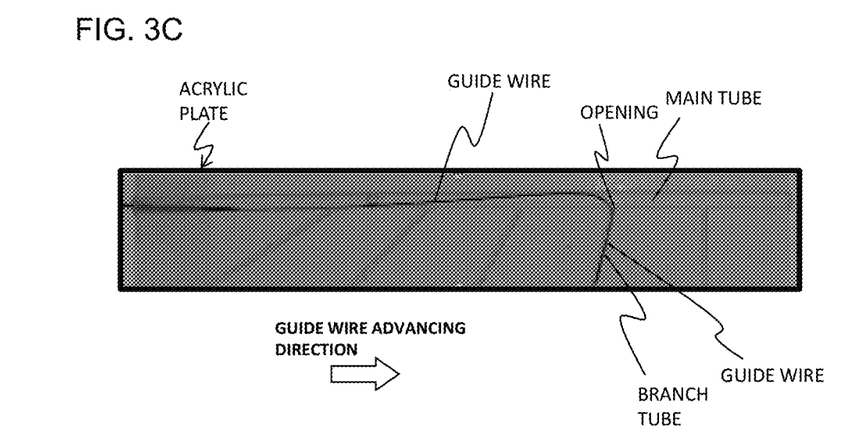
FIG. 3C is a schematic view illustrating a state of an advancing guide wire, and is the schematic view illustrating the guide wire having an inferior branch vessel aberrant insertion prevention property.

Here, when the guide wire does not advance deeply into the branch tube but advances along the main tube (see FIG. 3B, for example), the branch vessel aberrant insertion prevention property was evaluated as preferable "A", and when the guide wire is deepened from the opening into the branch tube (see FIG. 3C, for example), the branch vessel aberrant insertion prevention was evaluated as inferior "B".

TABLE 1

| | Outer diameter D1 of small diameter portion [mm] | Outer diameter D2 of large diameter portion [mm] | Length L of tapered portion [mm] | Bending rigidity ratio (FR1/FR2) [—] | Branch vessel aberrant insertion prevention property |
|---|---|---|---|---|---|
| Example 1 | 0.043 | 0.081 | 1.0 | 12.6 | A |
| Example 2 | 0.043 | 0.083 | 1.0 | 13.9 | A |
| Example 3 | 0.043 | 0.084 | 1.0 | 14.6 | A |
| Example 4 | 0.043 | 0.084 | 1.0 | 14.6 | A |
| Example 5 | 0.043 | 0.090 | 1.2 | 19.2 | A |
| Example 6 | 0.043 | 0.090 | 1.3 | 19.2 | A |
| Example 7 | 0.043 | 0.098 | 1.0 | 27.0 | A |
| Example 8 | 0.043 | 0.097 | 1.0 | 25.9 | A |

TABLE 1-continued

| | Outer diameter D1 of small diameter portion [mm] | Outer diameter D2 of large diameter portion [mm] | Length L of tapered portion [mm] | Bending rigidity ratio (FR1/FR2) [—] | Branch vessel aberrant insertion prevention property |
|---|---|---|---|---|---|
| Example 9 | 0.043 | 0.097 | 1.0 | 25.9 | A |
| Example 10 | 0.043 | 0.098 | 2.7 | 27.0 | A |
| Example 11 | 0.043 | 0.099 | 3.0 | 28.1 | A |
| Example 12 | 0.043 | 0.099 | 2.7 | 28.1 | A |
| Example 13 | 0.043 | 0.117 | 1.1 | 54.8 | A |
| Example 14 | 0.043 | 0.117 | 1.0 | 54.8 | A |
| Example 15 | 0.043 | 0.118 | 1.0 | 56.7 | A |
| Example 16 | 0.043 | 0.138 | 1.0 | 106.1 | A |
| Example 17 | 0.043 | 0.139 | 1.2 | 109.2 | A |
| Example 18 | 0.043 | 0.140 | 1.1 | 112.4 | A |
| Example 19 | 0.051 | 0.110 | 1.0 | 21.6 | A |
| Example 20 | 0.051 | 0.110 | 1.0 | 21.6 | A |
| Example 21 | 0.051 | 0.109 | 1.0 | 20.9 | A |
| Example 22 | 0.054 | 0.116 | 1.1 | 21.3 | A |
| Example 23 | 0.054 | 0.117 | 1.1 | 22.0 | A |
| Example 24 | 0.054 | 0.117 | 1.2 | 22.0 | A |
| Example 25 | 0.060 | 0.128 | 1.1 | 20.7 | A |
| Example 26 | 0.060 | 0.129 | 1.0 | 21.4 | A |
| Example 27 | 0.034 | 0.075 | 1.3 | 23.7 | A |
| Example 28 | 0.039 | 0.075 | 1.0 | 13.7 | A |
| Example 29 | 0.032 | 0.085 | 1.1 | 49.8 | A |
| Example 30 | 0.032 | 0.085 | 1.4 | 49.8 | A |
| Example 31 | 0.033 | 0.085 | 1.1 | 44.0 | A |
| Example 32 | 0.032 | 0.093 | 1.6 | 71.3 | A |
| Example 33 | 0.032 | 0.093 | 1.1 | 71.3 | A |
| Example 34 | 0.032 | 0.093 | 1.6 | 71.3 | A |
| Example 35 | 0.036 | 0.093 | 1.3 | 44.5 | A |
| Example 36 | 0.039 | 0.093 | 1.2 | 32.3 | A |
| Example 37 | 0.037 | 0.093 | 1.4 | 39.9 | A |

TABLE 2

| | Outer diameter D1 of small diameter portion [mm] | Outer diameter D2 of large diameter portion [mm] | Length L of tapered portion [mm] | Bending rigidity ratio (FR1/FR2) [—] | Branch vessel aberrant insertion prevention property |
|---|---|---|---|---|---|
| Comparative Example 1 | 0.043 | 0.052 | 1.4 | 2.1 | B |
| Comparative Example 2 | 0.043 | 0.051 | 1.3 | 2.0 | B |
| Comparative Example 3 | 0.043 | 0.051 | 1.2 | 2.0 | B |
| Comparative Example 4 | 0.040 | 0.056 | 1.2 | 3.8 | B |
| Comparative Example 5 | 0.043 | 0.059 | 1.1 | 3.5 | B |
| Comparative Example 6 | 0.043 | 0.058 | 1.1 | 3.3 | B |
| Comparative Example 7 | 0.043 | 0.060 | 1.1 | 3.8 | B |
| Comparative Example 8 | 0.041 | 0.061 | 1.0 | 4.9 | B |
| Comparative Example 9 | 0.042 | 0.062 | 1.2 | 4.7 | B |
| Comparative Example 10 | 0.043 | 0.065 | 1.0 | 5.2 | B |
| Comparative Example 11 | 0.043 | 0.066 | 1.0 | 5.6 | B |
| Comparative Example 12 | 0.043 | 0.066 | 1.0 | 5.6 | B |
| Comparative Example 13 | 0.043 | 0.065 | 1.0 | 5.2 | B |
| Comparative Example 14 | 0.043 | 0.066 | 1.0 | 5.6 | B |
| Comparative Example 15 | 0.043 | 0.073 | 0.9 | 8.3 | B |
| Comparative Example 16 | 0.043 | 0.074 | 1.0 | 8.8 | B |
| Comparative Example 17 | 0.043 | 0.074 | 1.0 | 8.8 | B |

Figure 4:
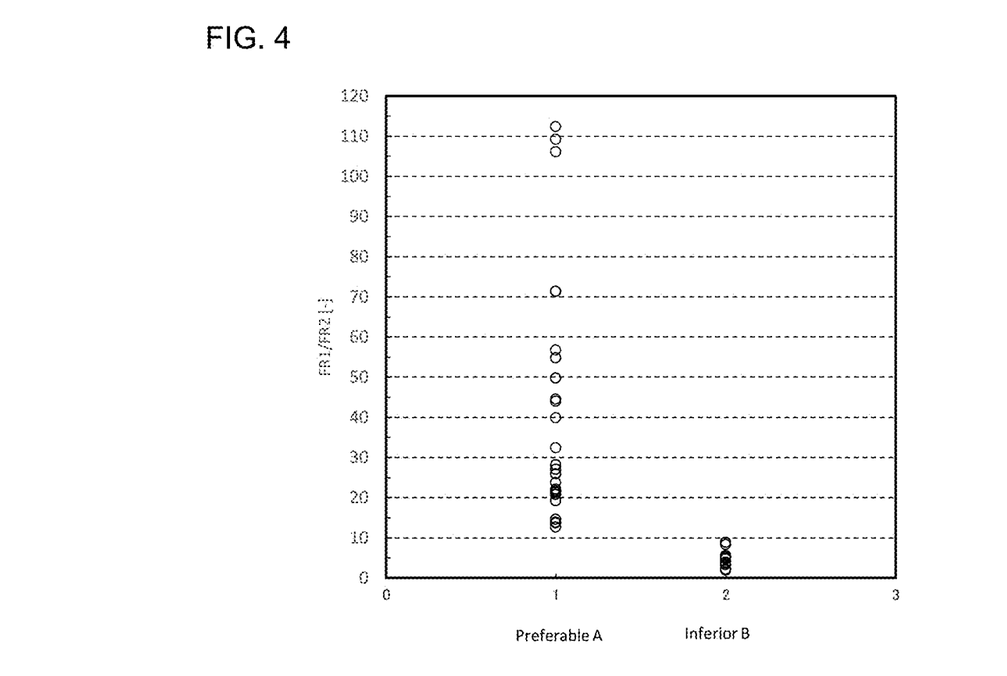
FIG. 4 is a graph in which the evaluation results of Tables 1 and 2 are plotted.

As can be seen from the results shown in Tables 1, 2 and FIG. 4, the branch aberrant insertion prevention property was preferable "A" in all of the examples, while it was inferior "B" in all of the comparative examples. That is, whether or not the branch pipe aberrant insertion prevention is preferable varies with the bending rigidity ratio (FR1/FR2)=10 as a lower limit, e.g., separating those examples that providing suitable branch aberrant insertion prevention and those that did not.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Obviously, numerous modifications and variations of the present invention are possible in light of the above teachings. It is therefore to be understood that within the scope of the appended claims, the invention may be practiced otherwise than as specifically described herein.

The invention claimed is:

1. A guide wire, comprising:
a core shaft that includes a distal end portion stepwisely decreasing in diameter toward a distal end direction;
a coil body wound to cover at least a part of an outer periphery of the diameter-decreased distal end portion; and
a distal end fixing portion that fixes the distal end of the core shaft and a distal end of the coil body to each other, wherein
the distal end portion of the core shaft includes:
a small diameter portion adjacent to the distal end fixing portion,
a large diameter portion that is positioned further in a proximal end direction than the small diameter portion and has a larger diameter than the small diameter portion, and
a tapered portion between the small diameter portion and the large diameter portion, the tapered portion gradually increasing in diameter from the small diameter portion toward the large diameter portion,
the core shaft and the coil body are fixed at a portion of the core shaft excluding the tapered portion, and
a first bending rigidity FR1 of the large diameter portion, a second bending rigidity FR2 of the small diameter portion, and a length L of the tapered portion in an axial direction of the core shaft satisfy the following expressions (1) and (2):

$$FR1/FR2 \geq 10 \qquad (1)$$

$$1 \leq L \leq 3 \qquad (2)$$

(in the above expressions (1) and (2), the unit of L is mm (millimeter)).

2. The guide wire according to claim 1, further comprising:
an inner coil body that is a multiple spiral coil inside the coil body so as to cover the core shaft, wherein
the core shaft and the inner coil body are fixed at a region excluding the tapered portion, the region being on the core shaft in a proximal end direction from the tapered portion, and the distal end fixing portion.

3. The guide wire according to claim 2, wherein at least one of the coil body and the inner coil body has a higher bending rigidity in the proximal end direction than in the distal end direction of the tapered portion in the axial direction of the core shaft.

4. The guide wire according to claim 2, wherein at least one of the coil body and the inner coil body has different wire diameters before and after the tapered portion.

5. The guide wire according to claim 2, wherein the core shaft includes a core shaft main body and a connection portion between the core shaft main body and the large diameter portion, and the core shaft and the inner coil body are fixed at the connection portion.

6. The guide wire according to claim 1, wherein the core shaft includes a core shaft main body and a connection portion between the core shaft main body and the large diameter portion, and the core shaft and the coil body are fixed at the connection portion.

7. The guide wire according to claim 1, wherein the coil body has a higher bending rigidity in the proximal end direction than in the distal end direction of the tapered portion in the axial direction of the core shaft.

8. The guide wire according to claim 1, wherein the coil body has different wire diameters before and after the tapered portion.

* * * * *

UNITED STATES PATENT AND TRADEMARK OFFICE
CERTIFICATE OF CORRECTION

PATENT NO. : 11,432,808 B2
APPLICATION NO. : 16/846445
DATED : September 6, 2022
INVENTOR(S) : Tsuge et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 367 days.

Signed and Sealed this
Fifth Day of March, 2024

Katherine Kelly Vidal
*Director of the United States Patent and Trademark Office*